United States Patent [19]

Shimada et al.

[11] Patent Number: 4,726,947
[45] Date of Patent: Feb. 23, 1988

[54] BACTERIAL CELL EXTRACT, PROCESS FOR PREPARING SAME, ANTITUMOR PREPARATION CONTAINING SAME, AND ADJUVANT PREPARATION CONTAINING SAME

[75] Inventors: Shizuo Shimada; Tadashi Sudo; Hitoshi Inoue, all of Mobara; Yoshio Furutani, Yokohama; Yoshikazu Fujisawa, Kamakura, all of Japan

[73] Assignee: Matsui Toatsu Chemicals, Inc., Japan

[21] Appl. No.: 271,647

[22] Filed: Jun. 8, 1981

Related U.S. Application Data

[63] Continuation of Ser. No. 14,914, Feb. 26, 1979, abandoned.

[30] Foreign Application Priority Data

Mar. 10, 1978 [JP] Japan .................. 53-26519

[51] Int. Cl.$^4$ .................. A61K 39/02; A61K 35/78
[52] U.S. Cl. .................. 424/92; 424/195.1
[58] Field of Search .................. 424/92, 195

[56] References Cited

U.S. PATENT DOCUMENTS

| | | | |
|---|---|---|---|
| 3,399,263 | 8/1968 | Strazdins et al. | 424/92 |
| 3,600,378 | 8/1971 | Marsh et al. | 424/92 |
| 3,790,665 | 2/1974 | Glass et al. | 424/92 |
| 3,956,481 | 5/1976 | Jolles et al. | 424/92 |
| 3,976,544 | 8/1976 | Adam et al. | 424/92 |
| 4,001,395 | 1/1977 | Jolles et al. | 424/92 |

FOREIGN PATENT DOCUMENTS

| | | | |
|---|---|---|---|
| 1426042 | 2/1976 | United Kingdom | 424/92 |
| 552744 | 11/1977 | U.S.S.R. | 424/92 |

OTHER PUBLICATIONS

Lamensans et al., Proc. Nat. Acad. Sci., 72, pp. 3656-3660 (1975).
Azuma et al., J. of Nat. Cancer Inst., 52, pp. 95-100 (1974).
Adam et al., Proc. Nat. Acad. Sci., 69, pp. 851-854 (1972).
Weiss, Medical Clinics of N.A., vol. 60, No. 3, pp. 473-497 (1976).
Youmans et al, J. of Bacteriology, 99, pp. 42-50 (1969).

*Primary Examiner*—Jerome D. Goldberg
*Attorney, Agent, or Firm*—Sughrue, Mion, Zinn, Macpeak and Seas

[57] ABSTRACT

Cells of a microorganism, such as *Mycobacterium tuberculosis*, belonging to the genus Mycobacterium are disrupted in distilled water or a suitable buffer solution, and then centrifuged or filtrated to remove the cell wall residue. To the aqueous cell-free extract is added a polyvalent metal salt or an antibiotic, such as streptomycin sulfate, which acts as a flocculant to form a precipitate. The precipitate consists essentially of sugar, protein, lipid, and nucleic acid. Owing to its high antitumor and adjuvant activities as well as its slight side effects, it can be used as antitumor and adjuvant preparations.

7 Claims, No Drawings

BACTERIAL CELL EXTRACT, PROCESS FOR PREPARING SAME, ANTITUMOR PREPARATION CONTAINING SAME, AND ADJUVANT PREPARATION CONTAINING SAME

This is a continuation of application Ser. No. 014,914, filed 2/26/79, now abandoned.

BACKGROUND OF THE INVENTION

1. Field of the Invention

This invention relates to a bacterial cell extract prepared from disrupted cells of a microorganism belonging to the genus Mycobacterium, a process for preparing the same, an antitumor preparation containing the same, and an adjuvant preparation containing the same.

2. Description of the Prior Art

It is well known that the tubercle bacilli have a strong antitumor activity, and attempts have been made to administer living cells of the tubercle bacillus to patients with malignant tumor. However, the administration of living cells of the tubercle bacillus involves a great risk of infection and produces severe side effects such as ulceration and fever. For avoiding the risk of infection, a number of attempts have been made to extract the component with antitumor activity from the tubercle bacillus. The active substances so far prepared from the tubercle bacillus include hot-water extract, water-soluble adjuvant, wax, ribonucleic acid, cell wall skeleton, extracted cell residue with organic solvents, and the like.

However, these substances derived from the tubercle bacillus leave much to be improved. The substances having only slight side effects are not always high in antitumor activity, while those having a high antitumor activity tend to produce severe side effects such as hepatic or renal disturbances, fever, vomiting, and ulceration. Moreover, some substances require a complicated procedure for the preparation and the substances thus obtained are not always high in antitumor activity.

The present inventors have performed intensive and extensive studies of various extracts prepared from cells of the tubercle bacilli and related microorganisms, and have found quite unexpectedly that an active substance having a high antitumor activity and low toxicity can reproducibly be prepared with good yield on a simple procedure.

SUMMARY OF THE INVENTION

One object of this invention is to provide a bacterial cell extract prepared from disrupted cells of a microorganism belonging to the genus Mycobacterium. Another object of this invention is to provide a process for preparing such a bacterial cell extract. A further object of this invention is to provide an antitumor preparation containing such a bacterial cell extract as active ingredient. A further object of this invention is to provide an adjuvant preparation containing such a bacterial cell extract as active ingredient.

These and other objects of this invention are accomplished by providing a bacterial cell extract comprising a precipitate obtained by making an aqueous cell-free extract from disrupted cells of a microorganism belonging to the genus Mycobacterium and then adding a flocculant, as well as an antitumor and an adjuvant preparation containing such a bacterial cell extract as active ingredient.

DESCRIPTION OF THE PREFERRED EMBODIMENTS

The microorganism from which a substance having antitumor activity (hereinafter referred to as "N-1 substance") is prepared in accordance with this invention may be selected from the group of bacteria belonging to the genus Mycobacterium. Especially preferred examples of the microorganism include *Mycobacterium bovis*, BCG (Japanese strain), *Mycobacterium tuberculosis* Aoyama B and H37Ra, *Mycobacterium avium* IFO 3153 (No. of a strain deposite at Institute for Fermentation, Osaka), *Mycobacterium smegmatis* ATCC 607 (No. of a strain deposited at American Type Culture Collection) and the like.

No particular restrictions are imposed on the methods of growing the microorganism and preparing an active substance therefrom, and any conventional procedures that are suited to the type of microorganism used may be followed. For example, *Mycobacterium bovis* BCG is inoculated into a culture medium such as Sauton's medium or glycerin-bouillon medium. This culture medium is allowed to stand at approximately 37° C. for 3 to 8 weeks, and the resulting culture is filtered to obtain a mass of cells. These cells are suspended in water or preferably a suitable buffer solution, and then disrupted by means of a suitable apparatus such as Dyno-Mill or French press to form a disrupted cell suspension. For the disruption of the cells, it is preferable to maintain the temperature below 10° C., for example, by cooling with ice. If the temperature of the suspension exceeds 10° C. owing to the heat generated during disruption, the activity of the extracted component will be decreased by the action of enzymes. Preferred examples of the buffer solution include phosphate, borate acetate, citrate, tartrate, succinate, and tris(hydroxymethyl)aminomethane buffer solutions, and they may be used in a concentration of 0.001 to 1M and preferably 0.01 to 0.1M.

The disrupted cell suspension thus obtained is then filtrated or centrifuged to form an aqueous cell-free extract suitable for the preparation of an active substance. The term "aqueous cell-free extract" as used herein means the disrupted cell suspension from which the remaining intact cells and the cell wall residue have been removed as much as possible by filtration or centrifugation. Preferably, this separating operation is carried out so that the content of the cell wall skeleton in the final N-1 substance will not exceed 8%. In carrying out the separating operation, it is also preferable to maintain the temperature below 10° C. If the temperature exceeds 10° C., the active component of the aqueous cell-free extract will be deteriorated by the action of enzymes, and the separability thereof will be diminished.

The flocculant which is used to precipitate the N-1 substance from the cell-free extract may be selected from a wide variety of compounds. Preferred examples of the flocculants include polyvalent metal salts such as aluminum sulfate, calcium chloride, magnesium chloride, ferric chloride, and manganese chloride; synthetic polymer flocculants such as polyacrylamide and polyamine; natural water-soluble basic polymers such as chitosan and protamine sulfate, and sodium alginate; water-soluble basic antibiotics such as streptomycin and kanamycin, and salts thereof; and the like. The amount of flocculants used may be properly determined depending on the type thereof. For example, polyvalent metal salts are suitably used in concentration at 0.1 to 10% (weight percent of flocculant calculated with respect to the volume of cell free extract) and preferably 0.1 to 3% (W/V), synthetic polymer flocculants in concentration at 0.01 to 1% (W/V) and preferably 0.01 to 0.1% (W/V), natural water-soluble basic polymers and sodium alginate in concentration at 0.01 to 10% (W/V) and preferably 0.01 to 1% (W/V), and water-soluble basic antibiotics in concentration at 0.1 to 10% (W/V) and preferably 0.1 to 1% (W/V).

Then, the N-1 substance is precipitated from the aqueous cell-free extract by adding a flocculant as defined above. The precipitate is separated from the mother liquor by a suitable technique such as filtration or centrifugation. In the course of the formation of a precipitate and its separation from the mother liquor, it is also preferable to maintain the temperature below 10° C. After the addition of the flocculating agent, the mixture is preferably allowed to stand for several hours to form the precipitate well. The N-1 substance separated from the mother liquor by filtration or centrifugation can be directly used in some cases, but is preferably subjected to an additional treatment to remove the flocculant contained in the precipitate. This can be accomplished, for example, according to the following procedure. The N-1 substance collected as above is suspended in water or a suitable buffer solution. Then, the flocculant is removed from the resulting suspension by a suitable technique such as dialysis, gel filtration, or ultrafiltration. Finally, the suspension so treated is lyophilized to obtain a purified N-1 substance. For the purifying operation, the temperature is preferably maintained below 10° C. in order to prevent the active component from being inactivated by the action of enzymes. Preferred examples of the buffer solutions for the purification include phosphate, borate, acetate, citrate, tartrate, succinate, and tris(hydroxymethyl)aminomethane buffer solutions, and they may be used in a concentration of 0.001 to 2M and preferably 0.01 to 0.2M. The pH of the buffer solution may preferably range from 4 to 10. If the pH is lower than 4, the dispersibility of the N-1 substance will be so reduced that the flocculant cannot be removed satisfactorily, while if the pH is higher than 10, the N-1 substance will occasionally be decomposed. Where streptomycin is used as flocculating agent, its removal is facilitated by a buffer solution which contains sodium chloride in a concentration of 0.1 to 0.5M. The concentration of sodium chloride higher than 0.5M does not affect the further removal of the streptomycin. In the final step, the suspension is preferably lyophilized in order to avoid deterioration of the N-1 substance.

The N-1 substances prepared in accordance with this invention have a complicated composition and consist essentially of sugar, protein, lipid, and nucleic acid. The N-1 substances obtained with the various flocculants show no significant differences in composition and have consistently high antitumor activities and only slight degrees of toxicity and side effects, so that they can be used as the active ingredient of antitumor preparations. Moreover, they can be easily prepared with good yield. Thus, the N-1 substance will be useful as an antitumor agent.

The N-1 substances can be administered to animals in the forms of injectable solutions, either alone or in combination with an antigenic substance. The N-1 substances are capable of being suspended both in water and in oil.

For example, they can be used in the form of either suspensions in physiological saline, or emulsions (of the water-in-oil type) by dispersing these suspensions in a vegetable or a mineral oil, or emulsions (of the oil-in-water type) by suspending them directly in a vegetable or a mineral oil and then dispersing the resulting suspensions in physiological saline.

The dosage of the N-1 substances may be properly determined depending on the animal species, administration route, and administration schedule. In mice, they may be administered intraperitoneally in a dose of 1 to 50 mg per kg of body weight or subcutaneously in a dose of 2 to 200 mg per kg of body weight. In guinea pigs, they may be administered intraperitoneally in a dose of from 1 to 100 mg per kg of body weight or subcutaneosuly in a dose of 0.05 to 100 mg per kg of body weight.

The sites at which the N-1 substances are administered may be either within the tumor or remote from the tumor.

For various types of tumors, the N-1 substances may be used in a dose ranging from one-tenth to the same as the dose of living cells of BCG, thereby producing an antitumor effect similar to that of living cells of BCG. For example, the preferred dose which is effective against Line 10 hepatoma in strain 2 guinea pigs is 100 μg per animal for the N-1 substances and 1 mg per animal for living cells of BCG. This suggests that the active component of living cells of BCG is concentrated in the N-1 substances.

Moreover, the N-1 substances have a powerful antitumor activity on both solid tumors and ascites tumors. The types of tumors against which the N-1 substances are effective include, for example, Ehrlich ascites tumor and solid tumor, sarcoma 180 ascites tumor and solid tumor, melanoma B-16, and the others. Especially for Line 10 hepatoma in strain 2 guinea pigs, the N-1 substances not only inhibit the growth of the primary tumor but also prevent metastasis to the regional lymph nodes, thus leading to a complete cure. Moreover, the guina pigs reject second inoculation of Line 10, suggesting the establishment of the tumor specific immunity by the treatment of N-1 substances.

When the N-1 substances are subcutaneously administered to patients with malignant tumor, the effective dose is presumed to be not more than 1 or 2 mg per single injection.

Since the N-1 substances are prepared from an aqueous cell-free extract of mycobacterium such as BCG, they involve no risk of infection. At least as far as animals are concerned, the N-1 substances do not cause side effects, such as ulceration at the site of administration and hepatic or renal disturbances, as is usual with living cells of BCG. Moreover, the N-1 substances seldom cause an allergic reaction in tuberculin-sensitized animals. Furthermore, even if the N-1 substances are intraperitoneally administered to animals for one month in a daily dose equal to ten times that of living cells of BCG, the manifestation of toxic effects such as retardation of growth, death, anemia, hepatic disturbances, and inflammation is rare.

In addition, the N-1 substances has an adjuvant activity equal to or higher than that of killed cells of BCG. As well known, an adjuvant is a substance which is injected with an antigen, to an animal and enhances its immunological response to the antigen. Various microorganisms and cellular components have been hitherto examined for adjuvant activity. Among others, the tubercle bacillus is well known to have strong adjuvant activity, and has been used for immunological experiments. Recently, attempts have been made to utilize the adjuvant activity of tubercle bacilli or their cellular components in the immunotherapy of tumors.

However, if tubercle bacilli are administered to patients, a severe degree of side effects such as ulceration and fever are observed. Those cellular components of tubercle bacilli with adjuvant activity are not always low in toxicity. They often require a complicated procedure for the preparation.

The N-1 substances have a high adjuvant activity and very low toxicity. The N-1 substances with these properties are very useful in enhancing the tumor-specific immunity of tumor-bearing animals.

When used as adjuvant, the N-1 substances are administered to animals in the form of injectable solutions with an antigenic substances. As described above, the N-1 substances are capable of being suspended either in water or in oil.

For example, the N-1 substances can be used as adjuvants in the form of either supensions obtained by dispersing them, together with an antigenic substance, in physiological saline, or emulsions (of the water-in-oil type) obtained by dispersing these suspensions in a vegetable or a mineral oil, or emulsions (of the oil-in-water type) obtained by suspending them, together with an antigenic substance, in a vegetable or a mineral oil and then dispersing the resulting suspensions in physiological saline.

The dosage of the N-1 substances used as adjuvants may be preperly determined depending on the animal species, administration route, and administration schedule. In mice, they may be subcutaneously administered in a dose of 0.5 to 50 mg per kg of body weight, and in guinea pigs, they may be subcutaneously administered in a dose of 0.05 to 100 mg per kg of body weight.

The present invention will be more clearly understood by the following examples and experiments. The examples describe the methods of preparing N-1 substances and of making antitumor and adjuvant preparations from such N-1 substances. The experiments demonstrate the usefulness of such N-1 substances.

EXAMPLE 1

Active Substance Prepared from BCG

*Micobacterium bovis* BCG (Japanese strain) was inoculated into a glycerin-bouillon medium having the follwoing composition

| Composition | (g) |
| --- | --- |
| Bouillon | 20.0 |
| Potassium Phosphate | 0.5 |
| Citric Acid | 2.0 |
| Ammonium Ferric Citrate | 0.05 |
| Magnesium Sulfate | 0.5 |
| Glycerin | 60.0 |

Add water to make a total volume of 1,000 ml. and was cultured at 37° C. for 5 weeks. The culture was filtrated through cheese cloth and the collected cells was washed twice with distilled water.

Then, 2,230 g of these cells were suspended in 4.1 g of a 10 mM phosphate buffer solution (pH 7.0), using a Waring blender, and disrupted with a Dyno-Mill under cooling with ice. The disrupted cell suspension was centrifuged at 10,000×g for 20 minutes at 4° C. to remove the intact cells and the cell wall residue. 5.3 l of an aqueous cell-free extract was obtained.

To this extract was added 15.9 g of streptomycin sulfate. The mixture was stirred well and then allowed to stand overnight at 4° C. The precipitate so formed was collected by centrifugation at 10,000×g for 20 minutes at 4° C., and then suspended in 800 ml of a 10 mM phosphate buffer solution (pH 7.0) containing 0.5M of sodium chloride. This suspension was dialyzed with cellophane tubing at 4° C. for one day against 10 l of the same buffer solution, then at 4° C. for one day against a 10 mM phosphate buffer solution (pH 7.0), and finally at 4° C. for one day against distilled water. The suspension so treated was lyophilized to obtain 75 g of an active substance of the invention.

This active substance will hereinafter be referred to as "N-B-1".

EXAMPLE 2

Active Substances Prepared from *Mycobacterium bovis* with Various Flocculants

*Mycobacterium bovis* BCG (Japanese strain) was treated in the same manner as in Example 1. To 100 ml of the aqueous cell-free extract thus obtained was added each of various flocculants in the specified amount. The mixture was stirred well and then allowed to stand overnight at 4° C. The precipitate so formed was collected by centrifugation with cooling, and then suspended in 10 ml of a 10 mM phosphate buffer solution (pH 7.0). If the flocculants was an antibiotic or an inorganic salt, this suspension was dialyzed against distilled water and then lyophilized to obtain an active substance of the invention. If the flocculant was a natural or synthetic polymer, this suspension was directly lyophilized to obtain an active substance of the invention. The type and amount of flocculants used and the yield of active substances obtained are shown in Table 1. In spite of various flocculants used, the active substances showed no significant differences in yield or composition.

TABLE 1

Active Substances Prepared with Various Flocculating Agents

| | Flocculating Agent | Amount (g) | Active Substance Yield (g) | Active Substance Designation |
|---|---|---|---|---|
| Antibiotic | Kanamycin Sulfate | 0.3 | 1.32 | N-B-2 |
| Inorganic Salt | Aluminum Sulfate | 1.0 | 1.78 | N-B-3 |
| | Calcium Chloride | 1.0 | 1.43 | N-B-4 |
| | Ferric Chloride | 1.0 | 1.67 | N-B-5 |
| | Manganese Chloride | 1.0 | 1.24 | N-B-6 |
| Natural Polymer | Sodium Alginate | 0.1 | 1.62 | N-B-7 |
| | Chitosan | 0.1 | 1.95 | N-B-8 |
| | Protamine Sulfate | 0.1 | 1.55 | N-B-9 |
| Synthetic Polymer | Polyacrylamide | 0.03 | 1.26 | N-B-10 |
| | Polyamine | 0.03 | 1.80 | N-B-11 |

The trade names of the polymer flocculants shown in Table 1 are as follows: Sodium Alginate (Junsei Kagaku Co., Japan), Chitosan (Tokyo Kasei Kogyo Co., Japan), Protamine Sulfate (Sigma Chemical Co., U.S.A.), Accofloc N-700 (a plyacrylamide, Mitsui Cyanamide Co., Japan), and Accofloc C-577 (a polyamine, Mitsui Cyanamide Co., Japan).

EXAMPLE 3

Active Substance Prepared for *Mycobacterium tuberculosis*

*Mycobacterium tuberculosis* Aoyama B was inoculated into a glycerin-bouillon medium having the same composition as described in Example 1 and cultured at 37° C. for 8 weeks. The culture was killed by heating at 120° C. for 20 minutes, and then filtrated through cheese cloth. The collected cells was washed twice with distilled water.

Then, 267 g of these cells were suspended in 1.3 l of a 10 mM phosphate buffer solution (pH 7.0), and disrupted with a Dyno-Mill under cooling with ice. The disrupted cell suspension was centrifuged, at 20,000×g for 20 minutes at 4° C. to obtain 1.1 l of an aqueous cell-free extract.

To this extract was added 3.3 g of streptomycin sulfate. The mixture was stirred well and then allowed to stand overnight at 4° C. The precipitate so formed was collected by centrifugation, at 10,000×g for 20 minutes at 4° C., and then suspended in 100 ml of a 10 mM phosphate buffer solution (pH 7.0) containing 0.5M of sodium chloride. This suspension was dialized at 4° C. using cellophane tubing for one day against 2 l of the buffer solution as described above, at 4° C. for one day against 2 l of a 10 mM phosphate buffer solution (pH 7.0), and finally at 4° C. for one day against distilled water. The suspension so treated was lyophilized to obtain 6.2 g of an active substance of the invention This active substance will hereinafter be referred to as "N-T-1".

EXAMPLE 4

Active Substance Prepared from *Mycobacterium smegmatis*

*Mycobacterium smegmatis* ATCC 607 was inoculated into a glycerin-bouillon medium having the same composition as described in Example 1 and cultured at 37° C. for 3 days. The culture was centrifuged and the collected cells was washed twice with distilled water.

Then, 350 g of these cells were suspended in 1.75 l of a 10 mM phosphate buffer solution (pH 7.0) and disrupted with a Dyno-Mill under cooling with ice. The disrupted cell suspension was centrifuged, at 10,000×g for 20 minutes at 4° C. to obtain 1.5 l of an aqueous cell-free extract.

To 100 ml of the aqueous cell-free extract thus obtained was added each of various flocculants in the specified amount. The mixture was treated in the same manner as in Example 2 to obtain an active substance of the invention. The type and amount of flocculants used and the yield of active substances obtained are shown in Table 2. In spite of various type of flocculants used, the active substances showed no significant differences in yield or composition.

TABLE 2

Active Substances Prepared with Various Flocculants

|  | Flocculating Agent | Amount (g) | Active Substance Yield (g) | Designation |
|---|---|---|---|---|
| Antibiotic | Streptomycin Sulfate | 0.3 | 1.15 | N-S-1 |
|  | Kanamycin Sulfate | 0.3 | 1.02 | N-S-2 |
| Inorganic Salt | Aluminum Sulfate | 1.0 | 1.32 | N-S-3 |
|  | Calcium Chloride | 1.0 | 1.18 | N-S-4 |
|  | Ferric Chloride | 1.0 | 1.24 | N-S-5 |
|  | Manganese Chloride | 1.0 | 1.27 | N-S-6 |
| Natural Polymer | Sodium Alginate | 0.1 | 1.32 | N-S-7 |
|  | Chitosan | 0.1 | 1.41 | N-S-8 |
|  | Protamine Sulfate | 0.1 | 1.35 | N-S-9 |
| Synthetic Polymer | Polyacrylamide | 1.03 | 1.09 | N-S-10 |
|  | Polyamine | 0.03 | 1.16 | N-S-11 |

The trade names of the polymer flocculants shown in Table 2 are the same as described for Table 1.

EXAMPLE 5 Active Substances Prepared from *Mycobacterium avium*

*Mycobacterium avium* IFO 3153 was inoculated into a glycerin-bouillon medium having the same composition as described in Example 1 and cultured at 37° C. for 6 weeks. The culture was filtrated through cheese cloth and the collected cells were washed twice with distilled water.

Then, 293 g of these cells were suspended in 1.5 l of a 10 mM phosphate buffer solution (pH 7.0), and disrupted with a Dyno-Mill under cooling. The disrupted cell suspension was centrifuged, at 20,000×g for 20 minutes at 4° C. to obtain 1.2 l of an aqueous cell-free extract.

To this extract was added 3.6 g of streptomycin sulfate. The mixture was treated in the same manner as in Example 3 to obtain 8.7 g of an active substance of the invention.

This active substance will hereinafter be referred to as "N-A-1".

EXAMPLE 6

Preparation Containing N-1 Substance

Ten mg of N-B-1 was finely ground in a mortar with 0.5 ml of physiological saline. After addition of 25 ml of physiological saline, the mixture was stirred well to form a suspension of the N-1 substance in physiological saline.

EXAMPLE 7

Preparation Containing N-1 Substance

Ten mg of N-B-1 was homogenized with a small amount of Drakeol 6VR (Sanko Junyaku Co., Japan). After addition of 5 ml of physiological saline containing 0.2% of Tween 80, the mixture was homogenized to make an oil-in-water preparation containing the N-1 substance.

EXAMPLE 8

Preparation Containing N-1 Substance

Ten mg of N-B-1 was finely ground in a mortar with 2.5 ml of physiological saline. After addition of 2.5 ml of liquid paraffin containing 15% of Arlacel A (Sanko Janyaku Co., Japan), the mixture was homogenized to make a water-in-oil preparation containing the N-1 substance.

EXAMPLE 9

Preparation Containing N-1 Substance

Five mg of N-B-1 and 5 ml of liquid paraffin containing 15% of Tween 80 was homogenized to make an adjuvant preparation containing the N-1 substance.

Experiment 1

Composition of N-1 Substances

The composition of the N-1 substances is shown in Table 3. They were analyzed by the following methods.

(1) Sugar: Determined by the phenol-sulfate reaction (M. Dubois, K. A. Gilles, J. K. Hamilton, P. A. Rebers, and F. Smith: Analytical Chemistry, 28, 350, 1956).

(2) Protein: Determined by the modified method of Lowry (C. D. Stauffer: Analytical Biochemistry, 69, 646, 1975).

(3) Lipid: Determined by the method of Bleigh and Dyer (E. G. Bleigh and W. J. Dyer: Can. J. Biochem. Physiol., 37, 911, 1959).

(4) Nucleic Acid: Fractionated according to the procedure of Schmidt, Thannhauser and Schneider (W. C. Schneider: J. Biol. Chem., 164, 747, 1946) and determined by the diphenylamine reaction (K. Burton: Biochem. J., 62, 315, 1956) and by the orcinol reaction (W. Mejbaum: Z. Physiol. Chem., 258, 117, 1939).

TABLE 3

Composition of N-1 Substances

| Example | Sample Designation | Sugar | Protein | Lipid | Nucleic Acid |
|---|---|---|---|---|---|
| 1 | N-B-1 | 15.5 | 35.2 | 23.7 | 13.8 |
| 2 | N-B-6 | 16.3 | 35.4 | 24.5 | 10.8 |
| 2 | N-B-9 | 15.3 | 33.0 | 22.8 | 13.6 |
| 2 | N-B-11 | 14.5 | 16.1 | 22.9 | 7.2 |
| 3 | N-T-1 | 13.0 | 32.4 | 21.2 | 14.3 |
| 4 | N-S-1 | 14.8 | 33.0 | 23.5 | 10.5 |
| 4 | N-S-3 | 16.3 | 21.5 | 20.4 | 7.4 |
| 4 | N-S-7 | 21.2 | 30.7 | 22.1 | 4.0 |
| 4 | N-S-10 | 16.2 | 19.6 | 22.7 | 3.2 |
| 5 | N-A-1 | 14.6 | 35.0 | 18.3 | 8.9 |

It is evident from the data shown in Table 3 that the N-1 substances consist of sugar, protein, lipid, and nucleic acid in substantially constant proportions, independent of the various flocculants used.

Experiment 2

Muramic Acid Content of N-1 Substances

The muramic acid content of several N-1 substances was determined. Each N-1 substance was placed in a sealed tube and hydrolyzed with 6N hydrochloric acid at 100° C. for 5 hours. After the hydrolyzate was neutralized with sodium hydroxide, its muramic acid content was determined by the method of Hadžija (O. Hadžija: Analytical Biochemistry, 60, 512–517, 1974). The results are shown in Table 4.

TABLE 4

Muramic Acid Content of N-1 Substances

| Sample Designation | Muramic Acid Content (%) |
|---|---|
| N-B-1 | 0.6 |
| N-B-6 | 0.7 |
| Cell Wall Skeleton of BCG | 6.1 |
| 105,000 × g Supernatant Fraction of BCG | 0.5 |

For comparison, the muramic acid content of the cell wall skeleton and 105,000×g supernatant of BCG was determined. The cell wall skeleton was prepared by the method of Azuma et al (Journal of the National Cancer Institute 52, 95, 1974). The 105,000×g supernatant fraction was prepared by taking another portion of the same disrupted cell suspension, centrifuging it at 105,000×g for one hour, dialyzing the separated supernatant against distilled water, and then lyophilizing it. It is evident from the data shown in Table 4 that the N-1 substances contained scarcely any amount of cell wall residue.

Experiment 3

Content of cell wall skeleton in N-1 substance

Cell wall skeleton-like substance from the N-1 substance was prepared according to the method of I. Azuma et al [J. Natl. Can. Inst., 52,95–101 (1974)].

As a result, 0.22 g of cell wall skeleton-like substance was obtained from 5 g of N-B-1 and the yield was 4.4%.

From this data, it is evident that the N-1 substances contained scarcely any amount of cell wall.

Experiment 4

Antitumor Effect on Mouse Sarcoma

Using the procedure of Example 6, several antitumor preparations were made from active substances of the invention. Then, 0.5 ml of each preparation was intraperitoneally administered to 6 female mice of the ICR strain and, after 3 days, $2 \times 10^4$ cells of mouse sarcoma 180 were inoculated into the peritoneal cavity of each animal. After an additional 3 days, the same preparation was intraperitoneally administered in the specified dose. The number of the surviving animals was examined 30 days after the inoculation of tumor cells. The results are shown in Table 5.

The active substances of the invention were all found to supress the growth of tumor cells and to prolong the survival time of tumor-bearing animals. Moreover, no side effects were obserbed.

The physiological saline was used as control.

TABLE 5

Antitumor Effect on Mouse Sarcoma

| Sample Designation | Dose (μg/animal) | Number of Survivors/ Total Number of Animals |
|---|---|---|
| N-B-1 | 200 × 2 | 5/6 |
| N-T-1 | 200 × 2 | 6/6 |
| N-S-1 | 200 × 2 | 6/6 |
| N-A-1 | 200 × 2 | 5/6 |
| Living Cells of BCG | 1000 × 2 | 5/6 |
| Contorl | — | 0/6 |

Experiment 5

Antitumor Effect on Mouse Sarcoma

The antitumor effect of Several active substances of the invention on mouse sarcoma 180 was examined in the same manner as in Experiment 4. The results are shown in Table 6.

These active agents, which had been prepared with the various flocculants, were all found to have excellent antitumor effect.

TABLE 6

Antitumor Effect on Mouse Sarcoma

| Sample | Dose (μg/animal) | Number of Survivors/ Total Number of Animals |
|---|---|---|
| N-B-1 | 300 × 2 | 5/5 |
| N-B-3 | 300 × 2 | 4/5 |
| N-B-6 | 300 × 2 | 4/5 |
| N-B-7 | 300 × 2 | 4/5 |
| N-B-8 | 300 × 2 | 4/5 |
| N-B-9 | 300 × 2 | 4/5 |
| N-B-10 | 300 × 2 | 5/5 |
| N-B-11 | 300 × 2 | 4/5 |
| Living Cells of BCG | 1000 × 2 | 5/5 |
| Control | — | 0/5 |

Experiment 6

Antitumor Effect on Guinea Pig Hepatoma

Using the procedure of Example 7 and 8, several antitumor preparations were made from active substances of the invention. Then, $1 \times 10^6$ cells of Line 10 hepatoma syngeneic to strain 2 guinea pig were intradermally inoculated at the left flank of strain 2 guinea pigs in a group of five. When the diameter of the tumor reached approximately 10 mm, the specified amount of each preparation was injected into the tumor. Six weeks after the inoculation of tumor cells, the mean diameters of the primary tumor and the metastasis in the regional lymph node were measured. In addition, the number of the surviving animals was examined 8 weeks after inoculation. The results are shown in Table 7.

The active substances of the invention were inhibited the proliferation of the established tumor, and prevented metastasis, thus leading to a complete cure. No side effects were observed.

Living cells (referred to as "WC") of the microorganisms were tested for comparison. The oil-in-water and the water-in-oil preparations without the active substance were used as control.

TABLE 7

Antitumor Effect of N-1 Substances on Guinea Pig Hepatoma

| Microorganism used | Sample | Dose (μg/animals) | Number of survivors Total number of animals Ex-7* | Ex-8** | Mean diameter of primary tumor (mm) Ex-7* | Ex-8** | Mean diameter of metastatic tumor (mm) Ex-7* | Ex-8** |
| --- | --- | --- | --- | --- | --- | --- | --- | --- |
| Mycobacterium bovis BCG (Japanese) | N-B-1 | 200 | 4/5 | 5/5 | 5 | 0 | 10 | 0 |
|  | WC | 2,000 | 4/5 | 5/5 | 4 | 0 | 11 | 0 |
| Mycobacterium smegmatic ATCC 607 | N-S-1 | 200 | 3/5 | 4/5 | 14 | 10 | 14 | 11 |
|  | WC | 2,000 | 1/5 | 2/5 | 21 | 16 | 40 | 25 |
| Control | — | — | 0/5 | 0/5 | 23 | 25 | 52 | 60 |

*The preparations were made by the procedure of Example 7.
**The preparations were made by the procedure of Example 8.

Experiment 7

Antitumor Effect on Mouse Ehrlich Tumor

Using the procedure of Example 6, several antitumor preparations were made from active substances of the invention. 0.5 ml of each preparation was intraperitoneally administered to 6 femal mice of ddY strain and, 3 days later, $2 \times 10^4$ cells of Ehrlich tumor was inoculated into the peritoneal cavity of each animal. After an additional 3 days, the same preparation was intraperitoneally administered in the specified dose. The number of the surviving animals was examined 30 days after the inoculation of tumor cells. The results are shown in Table 8.

The active substances of the invention inhibited the growth of tumor cells, and prolonged the survival time of tumor-bearing animals. No side effects were observed.

The physiological saline was used as control.

TABLE 8

Antitumor Effect on Mouse Ehrlich Tumor

| Sample | Dose (μg/animal) | Number of Survivors/ Total Number of Animals |
| --- | --- | --- |
| N-B-1 | 300 × 2 | 4/6 |
| N-T-1 | 300 × 2 | 3/6 |
| N-S-1 | 300 × 2 | 3/6 |
| N-A-1 | 300 × 2 | 4/6 |
| Living BCG | 1000 × 2 | 3/6 |

TABLE 8-continued

Antitumor Effect on Mouse Ehrlich Tumor

| Sample | Dose (μg/animal) | Number of Survivors/ Total Number of Animals |
| --- | --- | --- |
| Control | — | 0/6 |

Experiment 8

Adjuvant Effect on Delayed-type Hypersensitivity

Using the procedure of Example 9, several adjuvant preparations were made from active substances of the invention. A solution of 100 mg of bovine serum albumin in 5 ml of physiological saline was added drop by drop to 5 ml of each preparation, and the resulting mixture was homogenized to make an water-in-oil emulsion. Then, 0.5 ml of the emulsion was intramuscularly administered to 4 female guinea pigs of Hartley strain of 5 week age. Four weeks later, a solution of 100 μg of bovine serum albumin in 0.05 ml of physiological saline was injected into the dorsal skin and the size (larger diameter × smaller diameter in mm) of the redness at the site of injection was measured after 48 hours. The average size of redness for each group is shown in Table 9.

A similar water-in-oil emulsion containing killed cells of BCG in place of the N-1 substance was used in the comparative group, and a similar water-in-oil emulsion without active substance was used in the control group.

The active substances of the invention were all found to have a remarkable adjuvant effect.

TABLE 9

Adjuvant Effect on Delayed-type Hypersensitivity

| Group | Sample | Size of Redness (mm × mm) |
| --- | --- | --- |
| Experimental Group | N-B-1 | 18 × 19 |
|  | N-B-6 | 16 × 17 |
|  | N-B-9 | 17 × 20 |
|  | N-B-11 | 16 × 19 |
|  | N-T-1 | 18 × 18 |
|  | N-S-1 | 17 × 16 |
|  | N-A-1 | 15 × 18 |
| Comparative Group | Killed Cells of BCG | 16 × 16 |
| Control | — | 5 × 6 |

Experiment 9

Adjuvant Effect on humoral Antibody Production

Several water-in-oil emulsions were prepared in the same manner as in Experiment 8. Then, 0.5 ml of each emulsion was administered intramuscularly to 4 female guinea pigs of Hartley strain of 5 week age. Four weeks after the injection, the antibody titer in serum against vovine serum albumin was determined by the quantitative precipitin reaction. The results are shown in Table 10.

A similar water-in-oil emulsion containing killed cells of BCG in place of the N-1 substance was used in the comparative group, and a similar water-in-oil emulsion without active substance was used in the control group.

The active substances of the invention were all found to have a remarkable adjuvant effect.

TABLE 10

| Group | Sample | Antibody Titer (μg N/ml) |
|---|---|---|
| Experimental Group | N-B-1 | 950 |
| | N-T-1 | 923 |
| | N-S-1 | 947 |
| | N-A-1 | 939 |
| Comparative Group | Killed BCG | 1,116 |
| Control | — | 230 |

Adjuvant Effect on Humoral Antibody Production

Experiment 10

Test of N-1 Substances for Tubercle Bacilli

Several N-1 substances were tested for the presence of living tubercle bacilli according to the procedure described in "A Guide to Tubercle Bacillus Test (1972)" (edited under the supervision of the Ministry of Health and Welfare, Japan).

To a suspension of each N-1 substance in sterile physiological saline was added a 1% sodium hydroxide solution. The resulting mixture was allowed to stand at 37° C. for 30 minutes and then neutralized with 15% sulfuric acid. 0.1 ml of the mixture was inoculated on a slant containing Ogawa's medium (Eiken Kagaku Co., Japan) allowed to stand at 37° C. for 3 weeks, and then the presence of colonies was examined. The results are shown in Table 11.

TABLE 11

Test of N-1 Substances for *Tubercle Bacilli*

| Sample Designation | Concentration (mg/ml) | Number of Colonies | Judgement |
|---|---|---|---|
| N-B-1 | 20 | 0 | Negative |
| N-T-1 | 20 | 0 | " |
| N-S-1 | 20 | 0 | " |
| N-A-1 | 20 | 0 | " |

It is evident that the active substances of the invention contain no living cells of the tubercle bacillus.

Experiment 11

Acute Toxicity

The N-1 substances were suspended in physiological saline and intraperitoneally administered to 6 male mice of ddY strain of 6 week age. Then, the LD50 (or median lethal dose) was determined. The results are shown in Table 12.

The N-1 substances were all found to have very low toxicity.

TABLE 12

Acute Toxicity of N-1 Substances

| Sample | LD50 (mg/kg) |
|---|---|
| N-B-1 | 900 |
| N-T-1 | 700 |

TABLE 12-continued

Acute Toxicity of N-1 Substances

| Sample | LD50 (mg/kg) |
|---|---|
| N-S-1 | 1,200 |
| N-A-1 | 1,000 |
| Killed BCG | 200–400 |
| Killed H37Ra | 200–400 |
| Killed *Mycobacterium smegmatis* | 200–400 |

Experiment 12

Subacute Toxicity

An N-B-1 substance was suspended in physiological saline, and was intraperitoneally administered, once a day, to 13 male and 13 female rats of JCL-SD strain of 6 week age. The administration was continued for 5 weeks in a daily dose of 100 mg per kg of body weight. For comparison, living cells of BCG were also tested in a daily dose of 10 mg per kg of body weight. Physiological saline alone was used in the control group. The changes in body weight of the male rats are shown in Table 13.

TABLE 13

Changes in Body Weight of Male Rats

| | Body Weight (g) | | | | | |
|---|---|---|---|---|---|---|
| | 0 | 1 | 2 | 3 | 4 | 5(week) |
| N-B-1 Substance (100 mg/kg) | 221 | 239 | 278 | 305 | 313 | 329 |
| Living BCG (10 mg/kg) | 223 | 234 | 323 | 339 | 301 | 293 |
| Control | 222 | 269 | 298 | 324 | 351 | 373 |

The N-B-1 substance (100 mg/kg) group and the BCG (10 mg/kg) group showed similar changes in body weight, except for the 2nd and 3rd weeks at which the values of the BCG (10 mg/kg) group were greater than those of the control group. These increases in body weight seem to be due to accumulation of abdominal ascites. The changes in body weight of the female rats were more or less similar.

During the experimental period, 3 animals died in the N-1 substance (100 mg/kg) group and 12 in the BCG (10 mg/kg) group. When living BCG were administered in a daily dose of 100 mg per kg of body weight, all animals died. As a result of examination made at the end of the experimental period, toxicities such as anemia, hepatic distrubances, and adhesion of intraperitoneal organs were distinctly observed in BCG (10 mg/kg) group, but the degree of these toxicities was very low in the N-B-1 substance (100 mg/kg) group.

What is claimed is:

1. A process for preparing a bacterial cell extract having anti-tumor activity comprising the steps of:
   (a) disrupting microorganism cells selected from the group consisting of *Mycobacterium bovis*, strain BCG (NIHJ) ATCC 19015, *Mycobacterium tuberculosis* RIMD Alyama B, *Mycobacterium tuberculosis* H37Ra ATCC 25177, *Mycobacterium smegmatis* IFO 3153 and *Mycobacterium smegmatis* ATCC 607, at a temperature below about 10° C. in order to prepare a disrupted cell suspension comprising an aqueous extract, undisrupted cells and cell wall residue;
   (b) removing the undisrupted cells and cell wall residue from the aqueous extract at a temperature below about 10° C. to produce an aqueous cell-free extract;
(c) adding to the aqueous cell-free extract, in order to form a precipitate and based on the volume thereof, a flocculant selected from the group consisting of:
  (i) polyvalent metal salts in an amount of from 0.1–10% by weight;
  (ii) polyacrylamides and polyamines in an amount of from 0.01–1.0% by weight;
  (iii) chitosan protamine sulfate and sodium alginate in an amount of from 0.01–10% by weight; and
  (iv) streptomycin and salts thereof and kanamycin and salts thereof in an amount of from 0.1–10% by weight,
(d) collecting the resulting precipitate;
(e) suspending the collected precipitate in water or in a suitable buffer solution;
(f) dialyzing the resulting suspension at a temperature below about 10° C. to remove the flocculant contained therein; and
(g) lyophilizing the dialyzed suspension.

2. The process as claimed in claim 1 wherein said flocculant is streptomycin sulfate.

3. A pharmaceutical composition useful as an adjuvant or anti-tumor agent comprising an anti-tumor theraputically effective amount of the precipitate obtained according to the process of claim 1 and a pharmaceutically acceptable carrier or diluent.

4. The pharmaceutical composition as in claim 3 wherein said carrier or diluent is selected from the group consisting of water, physiological saline and oil.

5. The pharmaceutical composition as in claim 3 wherein said carrier or diluent is physiological saline.

6. The pharmaceutical composition as in claim 3 wherein said composition is in the form of a water-in-oil emulsion or an oil-in-water emulsion.

7. The pharmaceutical composition as in claim 6 wherein said water-in-oil emulsion is prepared by suspending said precipitate in physiological saline and dispersing said suspension in a vegetable oil or mineral oil.

* * * * *

UNITED STATES PATENT AND TRADEMARK OFFICE
CERTIFICATE OF CORRECTION

PATENT NO. : 4,726,947

DATED : February 23, 1988

INVENTOR(S) : Shizuo Shimada et al

It is certified that error appears in the above-identified patent and that said Letters Patent is hereby corrected as shown below:

On the title page assignee should read

--(73) Assignee: Mitsui Toatsu Chemicals, Incorporated --.

Signed and Sealed this

Sixth Day of December, 1988

*Attest:*

DONALD J. QUIGG

*Attesting Officer*     *Commissioner of Patents and Trademarks*